United States Patent [19]

Wallach

[11] Patent Number: 4,917,951

[45] Date of Patent: Apr. 17, 1990

[54] LIPID VESICLES FORMED OF SURFACTANTS AND STEROIDS

[75] Inventor: Donald F. H. Wallach, Brookline, Mass.

[73] Assignee: Micro-Pak, Inc., Wilmington, Del.

[21] Appl. No.: 124,824

[22] Filed: Nov. 24, 1987

Related U.S. Application Data

[63] Continuation-in-part of Ser. No. 078,658, Jul. 28, 1987, Pat. No. 4,855,090.

[51] Int. Cl.$^4$ .................. A61K 9/66; A61K 37/22; B01J 13/02
[52] U.S. Cl. ............................. 428/402.2; 264/4.1; 264/4.4; 424/1.1; 424/7.1; 424/450; 436/829
[58] Field of Search ............... 428/402.2; 424/450; 436/829; 568/606; 252/DIG. 1

[56] References Cited

U.S. PATENT DOCUMENTS

| | | | |
|---|---|---|---|
| 3,372,201 | 3/1968 | Leary et al. | 252/DIG. 1 |
| 3,957,971 | 5/1976 | Oleniacz | 424/70 |
| 4,133,874 | 1/1979 | Miller et al. | 428/402.2 X |
| 4,217,344 | 8/1980 | Vanderberghe et al. | 424/60 |
| 4,241,046 | 12/1980 | Papahadjopoulos et al. | 424/450 X |
| 4,247,411 | 1/1981 | Vanderberghe et al. | 264/4.6 |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,485,054 | 11/1984 | Mezei et al. | 264/4.6 |
| 4,536,324 | 8/1985 | Fujiwara et al. | 252/311 |
| 4,551,288 | 11/1985 | Kelly | 264/4.6 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,684,625 | 8/1987 | Eppstein et al. | 514/19 |
| 4,692,433 | 9/1987 | Hostetler et al. | 514/12 |
| 4,695,554 | 9/1987 | O'Connell et al. | 436/528 |
| 4,725,442 | 2/1988 | Haynes | 514/816 X |
| 4,731,210 | 3/1988 | Weder et al. | 264/4.3 |
| 4,772,471 | 9/1988 | Vanlerberghe et al. | 424/450 |

FOREIGN PATENT DOCUMENTS

| | | |
|---|---|---|
| 0032578 | 7/1984 | European Pat. Off. |
| 3410602 | 9/1984 | Fed. Rep. of Germany |
| 59-106423 | 6/1984 | Japan |
| 61-207324 | 9/1986 | Japan |
| 1539625 | 6/1976 | United Kingdom |
| 2078543 | 1/1982 | United Kingdom |
| 2079179 | 1/1982 | United Kingdom |
| 2147263 | 9/1984 | United Kingdom |
| 2166107 | 4/1986 | United Kingdom |
| 8501440 | 10/1984 | World Int. Prop. O. |

OTHER PUBLICATIONS

"Bilayer Fluidity of non-ionic Vesicles, An Investigation by Differential Polarized Phase Fluorometry," Ribier and Handjani-Vila, Colloids and Surfaces, 10:155–161, (1984).

"Non-ionic Surfactant Vesicles, Niosomes, as a Delivery system for the Anti-leishmanial Drug, Sodium Stibogluconate," Baillie et al., J. Pharm. Pharmacol., 38:502–505, (1986).

"The Preparation and Properties of Niosomes-non-ionic Surfactant Vesicles," Baillie et al., J. Pharm. Pharmacol., 37:863–868, (1985).

"A very mild Method Allowing the Encapsulation of very High Amounts of Macromolecules into very Large (100 nm) Unilamellar Liposomes," Philippot et al., Biochem. Biophys. Acta, 734:137–143, (1983).

"Extemporaneous Preparation of Large Unilamellar Liposomes," Philippot et al., Biochem. Biophys. Acta, 821:79–84, (1985).

"Methodes de preparation des liposomes," Dousset and Douste-Blazy, *Les Liposomes*, Puisieux and Delattre, Eds. Techniques et Documentation La Voisier Paris, p. 41–72, (1985).

"Problemes technologiques poses par l'utilisation des liposomes comme vecteurs de substances medicamenteuses, Encapsulation, sterilisation, conservation," Puisieux and Poly, *Les Liposomes*, Puisieux and Delattre, Eds. Techniques et Documentation La Voisier Paris, p. 73–113, (1985).

"Procedure for Preparation of Liposomes with Large Internal Aqueous Space and High Capture by Reverse-Phase Evaporation," Szoka, Jr. and Papahadjopoulos, Proc. Natl. Acad. Sci. U.S.A., 75(9):4194–4198, (1978).

"Les niosomes," Handjani-Vila et al., *Les Liposomes*, Puisieux and Delattre, Eds. Techniques et Documentation La Voisier Paris, p. 297–313, (1985).

"Liposomes," Edited by Marc J. Ostro, The Liposome Co., Princeton, NJ, Marcel Dekker, Inc., New York, p. 246–249, (1983).

McCutcheon's *Detergents & Emulsifiers*–1973 No. American Edition Publ. by McCutchen's Division, Allured Publishing Co., Ridgewood, NJ, (1973), p. 27 [TP 990 .D4].

*Primary Examiner*—Richard D. Lovering
*Attorney, Agent, or Firm*—Lahive & Cockfield

[57] ABSTRACT

Disclosed is a method of making lipid vesicles of a steroid and surfactants which do not form vesicles in the absence of the steroid. The surfactants are polyoxyethylene derivatives of 16–20 carbon ethers and amines.

8 Claims, No Drawings

LIPID VESICLES FORMED OF SURFACTANTS AND STEROIDS

REFERENCE TO RELATED APPLICATIONS

This application is a continuation-in-part of U.S. patent application Ser. No. 078,658, filed July 28, 1987 and now U.S. Pat. No. 4,855,090.

BACKGROUND OF THE INVENTION

The present invention relates to the field of lipid vesicle technology. More particularly, the present invention discloses lipid vesicles made of surfactants and steroids, possibily with other additives, and a method for their manufacture.

Liposomes, or lipid vesicles made using phospholipids, have been known since at least 1965. There are three general types of lipid vesicles: multilamellar vesicles (MLV), onion-like structures having a series of substantially spherical shells formed of lipid bilayers interspersed with aqueous layers; large (greater than $0.45\mu$ diameter, preferably greater than $1\mu$ diameter) unilamellar vesicles (LUV) which have a lipid bilayer surrounding a large, unstructured aqueous phase; and small unilamellar vesicles (SUV) which are similar in structure to the LUV's except their diameters are less than $0.2\mu$. Because of the relatively large amount of lipid in the lipid bilayers of the MLV's, MLV's are considered best for encapsulation or transportation of lipophilic materials whereas the LUV's, because of their large aqueous/lipid volume ratio, are considered best for encapsulation of hydrophilic molecules, particularly macromolecules. SUV's have the advantage of small size, which allows relatively easy access to the cells of tissue, but their small volume limits delivery of hydrophilic or aqueous materials to trace amounts. SUV's are more useful in the transportation of lipophilic materials.

As noted, all of the early lipid vesicle studies used phospholipids as the lipid source for the bilayers. The reason for this choice was that phospholipids are the principal structural components of natural membranes. However, there are many problems using phospholipids for liposome structures. First, isolated phospholipids are subject to degradation by a large variety of enzymes. Second, the most easily available phospholipids are those from natural sources, e.g., egg yolk lecithin, which contain polyunsaturated acyl chains that are subject to autocatalyzed peroxidation. When peroxidation occurs, the liposome structure breaks down, causing premature release of encapsulated materials and the formation of toxic peroxidation byproducts. This problem can be avoided by hydrogenation but hydrogenation is an expensive process, thereby raising the cost of the starting materials. Third, cost is a problem associated with the use of phospholipids on a large scale. A kilogram of egg yolk lecithin pure enough for liposome production presently costs in excess of $40,000. This is much too high a cost for a starting material for most applications.

Because of the high cost and additional problems in using phospholipids, a number of groups attempted to use synthetic amphiphiles in making lipid vesicles. For example, Vanlerberghe and others working for L'Oreal have used a series of synthetic polymers, primarily polyglycerol derivatives, as alternatives to the phospholipids. Similarly, Kelly and a group at Sandoz, Inc. have tried aliphatic lipids.

Recently, there has been some indication, particularly from the L'Oreal group, that surfactants might be used to form the lipid bilayer in liposome-like multilamellar lipid vesicles. Both surfactants and phospholipids are amphiphiles, having at least one lipophilic acyl or alkyl group attached to a hydrophilic head group. Head groups in surfactants, which are attached to one or more lipophilic chains by ester or ether linkages, include hydrophilic molecules such as polyoxyethylene, sorbitan, and polyglycerol derivatives. Commercially available surfactants include the BRIJ family of polyoxyethylene acyl ethers, the SPAN sorbitan alkyl esters, and the TWEEN polyoxyethylene sorbitan fatty acid esters, all available from ICI Americas, Inc. of Wilmington, Del.

Substantially all of the surfactants tried for lipid vesicle formation have relatively short (eighteen or under) carbon chains. This is because as the carbon chains grow too long, the lipophilic or hydrophobic regions are bulky so they do not easily form close packed lipid bilayers.

The experiments reported in the literature using synthetic surfactants rather than phospholipids to make multilamellar lipid vesicles have not shown any improvement in the ability to encapsulate either small or large hydrophilic molecules nor is there any increased stability of the lipid vesicles. In particular, there is no indication that lipid vesicles manufactured with these synthetic materials are particularly useful to achieve the hydrophilic and macromolecule delivery objects sought.

No matter what starting material is used to form the MLV's, substantially all of the methods of vesicle production reported in the literature use either the original Bangham method, as described in Bangham et al., J. Mol. Biol., 13: 238-252 (1965), or a minor variation. This basic approach starts by dissolving the lipids, together with any other lipophilic substances including any cholesterol used, in an organic solvent. The organic solvent is removed by evaporation, either using heat or by passing a stream of an inert gas (e.g., nitrogen) over the dissolved lipid to remove the solvent. The residue is then slowly hydrated with an aqueous phase, generally containing electrolytes and any hydrophilic biologically active materials, to form large multilamellar lipid membrane structures. In some variations, different types of particulate matter or physical structures have been used during the evaporation step to change the properties of the lipophilic phase and assist in the formation of the lipid residue. The basis for the use of these particulates is that by changing the physical structure of the lipid residue, better vesicles may form upon hydration. Two recent review publications, Szoka and Papahdjopoulos, Ann. Rev. Biophys. Bioeng. 9: 467-508 (1980), and Dousset and Douste-Blazy, in Les Liposomes, Puisieux and Delattre, Editors, Tecniques et Documentation Lavoisier, Paris, pp. 41-73 (1985), summarizes many of the methods which have been used to make MLV's.

Onde the MLV's are made, it is helpful to determine the effectiveness of the process. Two common measurements for effectiveness of encapsulation are encapsulated mass and captured volume. Encapsulated mass is simply the mass of substance encapsulated per unit mass of lipid, normally given in g material encapsulated/g lipid, or merely as a percentage. The captured volume is a measure of the water content trapped within the vesicles. The captured volume is defined as the amount of the aqueous fraction inside the vesicle divided by the total amount of lipid in the vesicle, normally given in ml/g lipid.

Multilamellar lipid vesicles made using the classic materials and methods have low encapsulated mass for hydrophilic materials, normally in the order of 5-15%. In addition, the captured volume is normally in the order of 2-4 ml/g lipid. However, the encapsulated mass for lipophilic materials is much better. Therefore, multilamellar lipid vesicles made using these standard procedures are good for encapsulating lipophilic (hydrophobic) materials, but are not as good for hydrophilic encapsulation.

Small unilamellar vesicles have a very low captured volume (approximately 0.5 ml/g) and also a very low encapsulated mass for hydrophilic materials (0.5-1%). However, since the lipid bilayer constitutes 50-87% of the total volume, SUV's are excellent at transporting small quantities of lipophilic material. SUV's primary advantage is in transport of very small quantities of hydrophilic material to tissues where the MLV's or LUV's cannot reach.

Other problems associated with multilamellar lipid vesicles (including the small unilamellar vesiscles which are normally manufactured by sonication of the multilamellar vesicles) are the time of manufacture and expense. Using standard methods, the current processes are both slow and relatively inefficient in terms of material, leading to large expense problems because of the high cost of starter materials. For example, the presently used methods take 2-20 hours to manufacture multilamellar lipid vesicles, and the sonication required to break the multilamellar lipid structures into SUV's takes additional time. This slow processing is unwieldy and expensive for any large scale use of lipid vesicles.

LUV's were developed because of the problems in encapsulating large volumes and obtaining high encapsulated mass for hydrophilic materials. LUV's have large captured volumes (approximately 6-35 ml/g lipid) and high encapsulated mass for hydrophilic materials (70-80%), including macromolecules, but the large relative aqueous volume makes them not as efficient in encapsulating hydrophilic or lipophilic materials as MLV's. In fact LUV's have several problems, even for hydrophilic encapsulation. Since there is only a single lipid bilayer surrounding a large aqueous center, LUV's tend to be less stable then the other lipid vesicles and more easily subject to chemical degradation. Further, the low lipid/aqueous volume ratio makes it difficult to use LUV's for transport of, or targeting with, any lipophilic materials.

Accordingly, an object of the invention is to provide improved lipid vesicles using different materials than those previously known.

Another object of the invention is to provide a method for making lipid vesicles from materials which could not otherwise be used to form the vesicles.

A further object of the invention is to provide inexpensive lipid vesicles which have high uptake of liquid and hydrophilic materials and do not have problems of stability or excessive cost.

A still further object of the invention is to provide inexpensive lipid vesicles which could be used to carry a variety of hydrophilic or lipophilic materials.

These and other objects and features of the invention will be apparent from the following summary of the invention and the description.

SUMMARY OF THE INVENTION

The foregoing objects of the invention are achieved by the use of long chain length surfactants which form defined, stable vesicles only in the presence of relatively high concentrations of steroids, including sterols like cholesterol. Theoretically, the steroid modulates the packing of the surfactants by intercalating between surfactant molecules, allowing proper orientation of the chains which permits the lipid bilayers to form. However, the theory is not necessary to the present invention since the bilayers do form. The steroid also has the advantageous property of buffering thermotropic phase transition as temperatures are changed.

The invention features multilamellar lipid vesicles formed of a variety of polyoxyethylene aliphatic ether and amine surfactants blended with 20-50% by weight of a steroid, preferably a sterol such as cholesterol. Each of the surfactants has a polyoxyethylene hydrophilic head group linked, either through an ether or amine linkage, to an alkyl chain. For example, in a polyoxyethylene (10) cetyl ether, the cetyl chain is the alkyl chain and the polyoxyethylene (10) is the head group.

In one embodiment of the invention, the surfactants are selected from a group consisting of polyoxyethylene (n) cetyl ($C_{16}$ saturated) ethers or polyoxyethylene (n') cetyl amines, where n and n' each range from 5-10. In another embodiment, the surfactant is selected from a group consisting of polyoxyethylene (x, y, or z) stearyl ($C_{18}$ saturated), oleyl ($C_{18}$ single double bond) or linoleyl ($C_{18}$ two double bonds) ethers, each having 2-10 polyoxyethylene units per acyl chain (x, y, and z range from 2-10). In a further embodiment, the surfactant consists of polyoxyethylene (x', y', or z') stearyl, oleyl, or linoleyl amines having 5-10 polyoxyethylene units per alkyl chain (x', y', and z' range from 5-10).

In still another embodiment of the invention, the surfactant may be selected from a group consisting of polyoxyethylene (s) eicosamonoenoyl ($C_{20}$ single double bond) or polyoxyethylene (t) eicosadienoyl ($C_{20}$ two double bonds) ethers where s and t ranges from 2-10. The corresponding amines, polyoxyethylene (s') eicosamonoenoyl and polyoxyethylene (t') eicosadienoyl amines, having 5-10 polyoxyethylene units per alkyl group (s' and t' range from 5-10), can also be used for the lipid vesicles of the invention. It may also be possible to use other 20 carbon alkyl polyoxyethylene derivatives, either ethers or amines, having differing amounts of unsaturation depending on the specific location of the double bonds.

All of these surfactants can be made into lipid vesicles by the same, general process. First, a lipophilic phase is formed by blending the surfactant and steroid together. If any other lipophilic materials are to be incorporated in, or encapsulated within, the lipid vesicle, they are also included in the lipophilic mix at this time. In a preferred method, the temperature of the lipophilic phase is kept above the melting point of the surfactant in order to ease blending; in certain procedures with particular materials, this may not be necessary. The lipophilic phase is then combined with an excess of an aqueous phase under shear conditions which provide adequate mixing, e.g., liquid shear which is substantially equivalent to the flow rate of 5-30 m/s through a 1 mm radius orifice for the combined phases. It is also preferable that the reaction is carried out above the melting point of the surfactant but again, with sufficient shear, this is not necessary. If any hydrophilic materials are to be incorporated within the lipid vesicles, they should be added to the aqueous phase before combining with the lipophilic phase.

Preferred steroids are sterols such as cholesterol or hydrocortisone acetate but any other steroid having similar chemical and physical properties can be used. The steroid buffers the thermotropic phase transition of the membrane layer which insures optimal size and provides high stability, particularly stability near the transition temperature of the lipid. The steroid is also necessary for lipid bilayer formation.

For certain uses, the incorporation of a charge producing amphiphile, yielding a net positive or negative charge to the lipid vesicles, is helpful. The preferred negative charge producing materials are oleic acid, dicetyl phosphate, palmitic acid, cetyl sulphate, retinoic acid, phosphatidic acid, phosphatidyl serine, and mixtures thereof. In order to provide a net positive charge to the vesicles, long chain amines, e.g., stearyl amines or oleyl amines, long chain pyridinium compounds (e.g., cetyl pyridinium chloride), quaternary ammonium compounds, or mixtures of these can be used. A preferred positive charge material is hexadecyl trimethylammonium bromide, a potent disinfectant. The use of this disinfectant as a positive charge producing material within the vesicles provides a secondary advantage as the vesicles deteriorate; they act as a sustained release germicide carriers.

The vesicles may also include targeting molecules, either hydrophilic or amphiphilic, which can be used to direct the vesicles to particular targets in order to allow release of the material encapsulated in the vesicle at a specified biological location. If hydrophilic targeting molecules are used, they can be coupled directly or via a spacer to an OH residue of the polyoxyethylene portion of the surfactant, or they can be coupled, using state of the art procedures, to molecules such as palmitic acid or phosphatidyl ethanolamine. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides, (e.g., for hepatic galactosyl receptors), or charged glycolipids such as gangliosides.

Vesicles made using the methods of the present invention can be used in diagnostic testing, e.g., agglutination testing of immunological systems. The vesicles can also be used as markers or labels for visualization, e.g., swelling or shrinking in the presence of an immune reaction, or for radiography or NMR.

Hydrophilic materials which can be encapsulated include macromolecules, viruses, immunological adjuvants such as muramyl dipeptide, and lymphokines, peptide hormones such as insulin, calcitonin and glucagon, and pituitary hormones, growth factors such as angiogenic, epithelial and epidermal growth factors, lymphokines such as interleukin-2 and interferon, blood proteins such as hemoglobin and Factor VIII, water-soluble plant hormones and pesticides, radionucleotides, contrast dyes for radiological diagnosis, and antibiotics. Examples of lipophilic materials which can be encapsulated include steroid hormones, organic pesticides, fungicides, insect repellants, and lipophilic vitamins and derivatives. A more complete listing of the types of materials that could be used in lipid vesicles is included in an article by Gregoriadis, New Engl. J. Med. 295: 704–711 (1976).

The following description and examples more fully illustrate the invention.

DESCRIPTION OF PARTICULAR EMBODIMENTS

The present invention features multilamellar lipid vesicles formed of specific polyoxyethylene alkyl ethers or polyoxyethylene alkyl amines and 20–50% (weight/weight surfactant) of a steroid, preferably a sterol such as cholesterol. The invention further features a method for manufacturing these multilamellar lipid vesicles. By modifying the materials and processes, multilamellar lipid vesicles of high encapsulated mass and captured volume can be achieved. These vesicles are better suited to the encapsulation and delivery of hydrophilic materials, including macromolecules, than currently used lipid vesicles. Further, by using the most preferred materials, these vesicles appear to tolerate a broader range of pH than classic liposomes or other lipid vesicles and are not as susceptible to attack by oxidative systems, e.g., peroxidases and superoxide-generating systems of phagocytes.

The multilamellar lipid vesicles are also cheaper to make because of a lower cost of starting materials.

In broad terms, the multilamellar lipid vesicles of the invention are made by forming a lipophilic phase of the selected surfactant and the steroid then combining the lipophilic phase with an excess of an aqueous phase under shear mixing conditions. If a charge producing material is used in the vesicle formulation, it is incorporated into the lipophilic phase before the surfactant contacts the aqueous phase. In addition, any lipophilic material to be encapsulated is added at the same time.

In a preferred embodiment, the temperature of the lipophilic phase is kept above the melting point of the surfactant in order to provide easy blending. This lipophilic phase is then forced into contact with an excess of an aqueous phase using a shear mixing device. The aqueous phase is normally also kept above the melting temperature of the surfactant for ease is processing. If any hydrophilic materials are to be encapsulated within the lipid vesicles, they are included in the aqueous phase before the aqueous phase is mixed with the lipophilic phase.

One of the advantages of using the materials and processes of the present invention is that the surfactants used have relatively low melting points so materials which are temperature sensitive can be encapsulated without damage. This permits the present method and materials to be used for encapsulation of many active materials, particularly biologicals.

As noted, anionic or cationic amphiphiles can be incorporated into the vesicles to yield a net negative or positive charge. Charge producing materials stabilize the lipid structure and provide rapid dispersion. However, the present invention does not require incorporation of a charge producing amphiphile for lipid vesicles formation. Lipid vesicles formed of these materials do not aggregate under normal circumstances so the dispersive effect of net surface charge is not as necessary as with other materials. However, the charge producing material assists in obtaining high aqueous volume uptake. The amount of charge producing amphiphile does not have to be large; 0.5 moles % — 5 moles % (based on the concentration of the surfactant) is sufficient to provide proper charge to the vesicles.

Once the lipophilic phase is formed, it is necessary to hydrate it using a liquid shear mixing technique. There are a large variety of devices available on the market which can provide this type of mixing. Devices which could be used include a Biotechnology Development Corporation microfluidizer, a "French"-type press, or any other device which provides a high enough shear mixing force and the ability to handle heated, semiviscous lipids. If a very high shear device is used, it may be possible to microemulsify powdered lipids, under pressure, at a temperature below their normal melting points and still form the multilamellar lipid vesicles of the present invention.

A preferred shear mixing device has a mixing chamber in cylindrical form with four tangential jet inputs. Two of the inputs are used to input the lipophilic phase solution and the other two act as inputs for the aqueous phase. There are two pumps, one for each phase, and the opposite jets are attached to the respective pumps. This allows control of the speed of injection, the ratio of phases, and the amounts in the chamber at any time. The aqueous and lipophilic phases are injected into the cylindrical chamber tangentially at high pressure, causing rotation of the phases about the chamber and, consequentially, shear between the phases. The chamber has an axially located discharge tube, perpendicular to the plane of the tangential input ports, which allows lipid vesicles formed in the chamber to be removed. This allows the shear mixing device to act in continuous processing. Using this device and the materials of the invention, lipid vesicles are formed within seconds rather than the hours using conventional procedures.

Once the multilamellar lipid vesicles are formed, the size can be changed or the structure modified by sonication or mechanical shear. Devices for carrying this out, as well as the general procedures, are known to those skilled in the art and are commonly used in the liposome field.

If the multilamellar lipid vesicles of the present invention are used as a drug delivery system, there is no particular limitation on how they can be used. For example, the vesicles may be dispersed directly in suspension, in aerosol form, topically, or in a gel. If used for agglutination testing or some other type of marker use, either aqueous dyes or lipophilic dyes which are taken up directly into the vesicle, may be used.

In addition to use as a drug or macromolecule delivery system, the multilamellar lipid vesicles of the invention have substantial other uses. For example, the vesicles can be used as an adjuvant in order to improve the immunological response of injected material. In addition, the high aqueous volume allows the use of the multilamellar lipid vesicles of the invention as moisturizers or skin creams with advantageous results. The high captured volume/lipid ratio is such that more moisture is provided to the skin using the vesicles of the invention than is available from conventional skin care creams.

The invention will be more apparent from the following, non-limiting Examples.

EXAMPLE 1

In this Example, polyoxyethylene (10) cetyl ether was tested with varying concentrations of cholesterol to see whether lipid vesicles were formed.

TABLE 1

| Test Number | 1. | 2. | 3. | 4. | 5. | 6. |
|---|---|---|---|---|---|---|
| B56 (ML) | 0.5 | 0.5 | 0.5 | 0.5 | 0.5 | 0.5 |
| CHOL (MG) | 0.0 | 26 | 52 | 78 | 92 | 130 |
| WATER (ML) | 2.0 | 2.0 | 2.0 | 2.0 | 2.0 | 2.0 |

Table 1 lists the concentration of ingredients tested. The surfactant, designated B56 on the Table is Brij 56, is produced by ICI Americas, Inc. of Wilmington, Del., and is soluble in water. The designation CHOL stands for cholesterol, with the amount blended with the surfactant given in mg. This surfactant is a cetyl ether, specifically polyoxyethylene (10) cetyl ether and has a melting point of 31° C. Each test, designated 1-6, had a different amount of cholesterol. All other concentrations and procedures are unchanged from test to test.

The surfactant and cholesterol were heated and blended at 40° C., forming the lipophilic phase. The lipophilic phase was then placed into a 1 ml syringe and forcibly ejected, via a three-way stop cock, into a 5 ml syringe containing the aqueous phase, to 2 ml of a 5 mM phosphate buffer containing 150 mM, sodium chloride, pH 7.4. The phosphate buffer was also at 40° C. The process of injection of the lipophilic phase into the aqueous phase took less than five seconds. The resulting mixture was then forced into a second 5 ml syringe at a linear flow rate of approximately 10 cm/s through an orifice about 1 mm in diameter. The mixture was continuously driven back and forth between the two 5 ml syringes for approximately two minutes, providing the mixing necessary to make lipid vesicles. The material was then transferred to a tube with 2 ml of Ficol/Hypaque gradient and centrifuged for ten minutes at 16,000 rpm in a Spinco U3 ultracentrifuge. This step separates the unencapsulated aqueous material from the lipid. The aqueous infranatant is then removed by piercing the centrifuge tube with a 20 gauge needle and withdrawing the liquid with a syringe.

When low cholesterol levels are used, e.g., 0% or 10% by weight cholesterol, lipid vesicles were not observed but rather a thin film of the lipid was seen on top of the aqueous phase after separation. However, at 20% cholesterol, a mixture of thin film and lipid vesicle formation was observed while at higher cholesterol concentrations (30, 40, and 50%), substantially all of the lipid was in the form of lipid vesicles. This was accompanied by substantial uptake of water into the vesicles. This experiment illustrates that using the methods and procedures of the present invention, specifically the incorporation of sufficient cholesterol into the lipophilic phase, vesicles can be made from materials which would not otherwise form lipid vesicles.

EXAMPLE 2

In this Example, dye and water uptake was measured for lipid vesicles. Brij 93, a polyoxyethylene (2) oleyl ether surfactant, was used as the basic material for the vesicles. Unlike the saturated $C_{16}$ carbon chain of the cetyl ether, this $C_{18}$ carbon chain is unsaturated with one double bond. The surfactant is a liquid at room temperature.

Table 2 shows the concentrations of materials tested. As with Example 1, these values correspond to 0–50% cholesterol by weight. The dye is calcein, a water-soluble dye mixed in as part of the aqueous phase.

TABLE 2

| Test Number | 1. | 2. | 3. | 4. | 5. | 6. |
|---|---|---|---|---|---|---|
| B93 (ML) | 0.5 | 0.5 | 0.5 | 0.5 | 0.5 | 0.5 |
| CHOL (MG) | 0.0 | 42 | 84 | 126 | 168 | 210 |
| WATER (ML) | 1.0 | 1.0 | 1.0 | 1.0 | 1.0 | 1.0 |
| CALCEIN (MG) | 0.2 | 0.2 | 0.2 | 0.2 | 0.2 | 0.2 |

The procedures used to form the lipid vesicles were identical to those described in Example 1.

TABLE 3

| Test Number | 1. | 2. | 3. | 4. | 5. | 6. |
|---|---|---|---|---|---|---|
| INFRA VOL (ML) | 1.6 | 1.5 | 1.5 | 1.0 | 0.95 | 0.95 |
| LAYER VOL (ML) | 0.9 | 1.0 | 1.0 | 1.5 | 1.6 | 1.6 |
| WATER UPTAKE (ML) | 0.4 | 0.5 | 0.5 | 1.0 | 1.1 | 1.1 |

Table 3 shows the results of this testing. The line infra volume shows that, as the cholesterol is increased, the infranatant volume declines and the lipid vesicle volume increases because water is transferred to the vesicles. As with Example 1, at the 20% cholesterol figure, a mixture of lipid vesicles and thin lipid film was observed. Below 20% cholesterol, only the thin film developed while above 20% cholesterol, only lipid vesicles, no free lipid, was observed. The results for dye uptake into the lipid vesicles, as measured spectophotometrically, correspond exactly to the water uptake figures, with more dye encapsulated as the proportion of cholesterol is increased.

TABLE 4

| Surfactant | Cholesterol | Mixture |
|---|---|---|
| Polyoxyethylene (10) Cetyl Ether | − | Solution |
| Polyoxyethylene (10) Cetyl Ether | + | Lipid Vesicles |
| Polyoxyethylene (2) Stearyl Ether | − | Gel |
| Polyoxyethylene (2) Stearyl Ether | + | Lipid Vesicles |
| Polyoxyethylene (4) Stearyl Ether | − | Gel |
| Polyoxyethylene (4) Stearyl Ether | + | Lipid Vesicles |
| Polyoxyethylene (10) Stearyl Ether | − | Gel |
| Polyoxyethylene (10) Stearyl Ether | + | Liposome |
| Polyoxyethylene (20) Stearyl Ether | − | Gel |
| Polyoxyethylene (20) Stearyl Ether | + | Gel |
| Polyoxyethylene (2) Oleyl Ether | − | Separate Bulk Phases |
| Polyoxyethylene (2) Oleyl Ether | + | Lipid Vesicles |
| Polyoxyethylene (5) Oleyl Ether | − | Separate Bulk Phases |
| Polyoxyethylene (5) Oleyl Ether | + | Lipid Vesicles |
| Polyoxyethylene (10) Oleyl Ether | − | Separate Bulk Phases |
| Polyoxyethylene (10) Oleyl Ether | + | Lipid Vesicles |
| Polyoxyethylene (5) Oleyl Amine | − | Turbid Solution |
| Polyoxyethylene (5) Oleyl Amine | + | Lipid Vesicles |
| Polyoxyethylene (2) Oleyl Amine | − | Turbid Solution |
| Polyoxyethylene (2) Oleyl Amine | + | Turbid Solution |

EXAMPLE 3

This Example illustrates that a variety of different molecules within the scope of the invention can be used to form the lipid vesicles. In this Example, a number of different sufficient materials were tested for vesicle formation using identical procedures except the presence or absence of 30% by weight cholesterol. Table 4 lists the materials tested and the results.

A negative sign (−) means that no cholesterol was used while a positive sign (+) means that 30% cholesterol (weight/weight surfactant) was used.

As is evident from this Example, adding a sterol such cholesterol in sufficient quantities can change the properties of the surfactant and allow lipid vesicles to be formed. This change is unexpected from anything previously known.

These Examples are meant to be illustrative only and not the limit of the invention. The invention is defined by the following claims.

What is claimed is:

1. A multilamellar lipid vesicle formed of surfactant materials which do not form vesicles in the absence of a steroid, said multilamellar lipid vesicle consisting essentially of a single surfactant selected from the group consisting of:
polyoxyethylene (n) cetyl ethers where n ranges from 5–10; polyoxyethylene (x) stearyl ethers where x ranges from 2–10; polyoxyethylene (y) oleyl ethers where y ranges from 2–10; polyoxyethylene (z) linoleyl ethers where z ranges from 2–10; polyoxyethylene (s) eicosamonoenoyl ethers where s ranges from 2–10; polyoxyethylene (t) eicosadienoyl ethers where t ranges from 2–10; and
about 20–50% of a steroid.

2. The lipid vesicle of claim 1 wherein said steroid comprises a sterol.

3. The lipid vesicle of claim 1 wherein said steroid is selected from a group consisting of cholesterol and hydrocortisone acetate.

4. The lipid vesicle of claim 1 further comprising a charge producing amphiphile.

5. A multilamellar lipid vesicle formed of surfactant materials which do not form these vesicles in the absence of a steroid, said multilamellar lipid vesicle consisting essentially of a single surfactant selected from the group consisting of:
polyoxyethylene (n') cetyl amines where n' ranges from 5–10; polyoxyethylene (x') stearyl amines where x' ranges from 5–10; polyoxyethylene (y') oleyl amines where y' ranges from 5–10; polyoxyethylene (z') linoleyl amines where z' ranges from 5–10; polyoxyethylene (s') eicosamonoenoyl amines where s' ranges from 5–10; polyoxyethylene (t') eicosadienoyl amines where t' ranges from 5–10; and
about 20–50% of a steroid.

6. The lipid vesicle of claim 5 wherein said steroid comprises a sterol.

7. The lipid vesicle of claim 5 wherein said steroid is selected from the group consisting of cholesterol and hydrocortisone acetate.

8. The lipid vesicle of claim 5 further comprising a charge producing amphiphile.

* * * * *